(12) United States Patent
Yamashita et al.

(10) Patent No.: US 9,198,584 B2
(45) Date of Patent: Dec. 1, 2015

(54) BLOOD PRESSURE MEASUREMENT DEVICE AND CONTROL METHOD FOR BLOOD PRESSURE MEASUREMENT DEVICE

(71) Applicant: OMRON HEALTHCARE Co., Ltd., Muko-shi, Kyoto (JP)

(72) Inventors: Yuki Yamashita, Kyoto (JP); Tatsuya Kobayashi, Kyoto (JP); Toshihiko Ogura, Kyoto (JP); Yoshihiko Sano, Kyoto (JP); Yukiya Sawanoi, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 14/371,795

(22) PCT Filed: Oct. 26, 2012

(86) PCT No.: PCT/JP2012/077710
§ 371 (c)(1),
(2) Date: Jul. 11, 2014

(87) PCT Pub. No.: WO2013/108460
PCT Pub. Date: Jul. 25, 2013

(65) Prior Publication Data
US 2015/0094602 A1 Apr. 2, 2015

(30) Foreign Application Priority Data
Jan. 16, 2012 (JP) .................................. 2012-006089

(51) Int. Cl.
*A61B 5/02* (2006.01)
*A61B 5/0225* (2006.01)
(Continued)

(52) U.S. Cl.
CPC ............ *A61B 5/0225* (2013.01); *A61B 5/02141* (2013.01); *A61B 5/02225* (2013.01); *A61B 5/02233* (2013.01)

(58) Field of Classification Search
None
See application file for complete search history.

(56) References Cited

U.S. PATENT DOCUMENTS 6,215,466 B1   4/2001   Yamazaki et al.
6,428,134 B1 *  8/2002  Clark et al. ..................... 347/10
(Continued)

FOREIGN PATENT DOCUMENTS

JP    05-100630 A    4/1993
JP    05-146414 A    6/1993
(Continued)

OTHER PUBLICATIONS

Official Communication issued in International Patent Application No. PCT/JP2012/077710, mailed on Jan. 29, 2013.

*Primary Examiner* — Navin Natnithithadha
*Assistant Examiner* — Michael R Bloch
(74) *Attorney, Agent, or Firm* — Keating & Bennett, LLP

(57) ABSTRACT

A control amplitude and a control frequency of a voltage applied to a piezoelectric pump are determined, control is carried out so that a voltage at the determined control amplitude and control frequency is applied to the piezoelectric pump, and a blood pressure value is calculated based on a cuff pressure detected by a pressure detection unit during inflation when the cuff pressure is increased by the piezoelectric pump. The amplitude of the voltage is controlled in predetermined steps, and a voltage having an amplitude that is a value above the control amplitude by at least one step and a voltage having an amplitude that is a value below the control amplitude by at least one step are applied, in a predetermined order, so that the control is essentially the same as when a voltage at the determined control amplitude is applied.

6 Claims, 8 Drawing Sheets

(51) Int. Cl.
*A61B 5/021* (2006.01)
*A61B 5/022* (2006.01)

(56) References Cited

U.S. PATENT DOCUMENTS

| | | | |
|---|---|---|---|
| 2005/0225202 A1* | 10/2005 | Vogeley et al. | 310/317 |
| 2009/0243431 A1* | 10/2009 | Ohsawa | 310/317 |
| 2010/0181867 A1 | 7/2010 | Inoue et al. | |
| 2010/0331667 A1* | 12/2010 | Nelson | 600/411 |
| 2011/0071409 A1* | 3/2011 | Hu et al. | 600/490 |
| 2012/0215118 A1* | 8/2012 | Chen et al. | 600/490 |

FOREIGN PATENT DOCUMENTS

| | | |
|---|---|---|
| JP | 2009-074418 A | 4/2009 |
| JP | 2010-162487 A | 7/2010 |
| JP | 2010-255447 A | 11/2010 |

* cited by examiner

TIME

BLOOD PRESSURE MEASUREMENT DEVICE AND CONTROL METHOD FOR BLOOD PRESSURE MEASUREMENT DEVICE

BACKGROUND OF THE PRESENT INVENTION

1. Field of the Invention

The present invention relates to blood pressure measurement devices and control methods for blood pressure measurement devices, and particularly relates to blood pressure measurement devices configured to measure a blood pressure during inflation of a cuff and to control methods for such blood pressure measurement devices.

2. Description of the Related Art

An electronic blood pressure meter that uses an oscillometric technique is known as a typical electronic blood pressure meter. In an electronic blood pressure meter that uses the oscillometric technique, a manchette containing an air bladder is uniformly wrapped around a part of a body, and changes in the volume of an arterial vessel pressurized by inflating/deflating the air bladder with air are obtained as changes in the amplitude of the pressure in the air bladder (a cuff pressure), which are then used to calculate a blood pressure. To measure the blood pressure accurately while inflating the cuff, it is necessary to properly control the speed at which the pressure within the cuff is increased. For example, it is necessary to inflate the cuff at a constant speed.

JP 2009-74418A proposes a piezoelectric micro-pump driven using a piezoelectric element, and discusses applying such a micro-pump in an electronic blood pressure meter. Meanwhile, JP 2010-255447A, JP 2010-162487A, and so on propose setting a driving frequency according to the material of a piezoelectric element and a diaphragm and carrying out control near the driving frequency.

Although conventional blood pressure meter pumps control pump output through pulse width modulation (PWM) control, piezoelectric pump output control is generally considered to be performed by driving the pump at the driving frequency and controlling the output through voltage control. However, such piezoelectric pumps have had the following problems: (1) the precision of voltage control corresponds to the precision of the pump output, and it is thus necessary to increase the precision of voltage control in order to control the inflation speed at a proper speed; (2) attempting to increase the precision of voltage control results in an increase in the number of components and the like for setting the resolution, leading to an increase in circuitry costs; and (3) although increasing the resolution by adding AM modulation to the voltage control can be considered, such a system is affected by pulsations, ambient sounds, and the like when installed in a blood pressure meter.

SUMMARY OF THE PRESENT INVENTION

Preferred embodiments of the present invention provide a blood pressure measurement device and a control method for such a blood pressure measurement device that, when controlling inflation using a piezoelectric pump during inflation for blood pressure measurement, are capable of increasing the precision of blood pressure measurement by suppressing the occurrence of noise, reducing the influence of pulsations, and controlling inflation at a high level of precision.

A blood pressure measurement device according to a preferred embodiment of the present invention includes a cuff that is configured to, when worn on a blood pressure measurement area, pressurize an artery in the measurement area at the pressure of a fluid in the cuff, a piezoelectric pump configured to increase the pressure within the cuff, a deflating unit configured to reduce the pressure within the cuff, a pressure detection unit configured to detect the cuff pressure that is the pressure within the cuff, and a control unit.

The control unit is configured and programmed to include a determination unit that determines a control amplitude and a control frequency of a voltage applied to the piezoelectric pump, an applied voltage control unit that carries out control so that a voltage at the control amplitude and control frequency determined by the determination unit is applied to the piezoelectric pump, and a blood pressure measurement unit that calculates a blood pressure value based on the cuff pressure detected by the pressure detection unit during inflation when the cuff pressure is increased by the piezoelectric pump. The applied voltage control unit is preferably configured and programmed to control the amplitude of the voltage in predetermined steps, and applies, in a predetermined order, a voltage having an amplitude that is a value that is above the control amplitude by at least one step and a voltage having an amplitude that is a value that is below the control amplitude by at least one step so that the output of the piezoelectric pump is approximately the same as when a voltage at the control amplitude determined by the determination unit is applied.

Preferably, the applied voltage control unit applies voltages having two amplitude values in an alternating manner. The two values include a value a predetermined step above and a value a predetermined step below the control amplitude determined by the determination unit, respectively. The control unit further includes an application ratio determination unit that, based on the control amplitude determined by the determination unit and the two values, determines a ratio of time for which the voltages at the two values are applied in an alternating manner so that the output of the piezoelectric pump is essentially the same as in the case where a voltage at the control amplitude is applied. The applied voltage control unit applies the voltages having two amplitude values according to the ratio of time determined by the application ratio determination unit.

Further preferably, the applied voltage control unit applies the voltages so that a difference between the two values is a minimum.

Preferably, the applied voltage control unit is configured and programmed to apply the voltages having two amplitude values determined by the determination unit in an alternating manner at the same ratio of time. The control unit further includes an applied voltage determination unit that, based on the control amplitude determined by the determination unit, determines the value a step above the control amplitude and the value a step below the control amplitude so that the output of the piezoelectric pump is essentially the same as in the case where a voltage at the control amplitude is applied. The applied voltage control unit is configured and programmed to apply the voltages having two amplitude values, determined by the applied voltage determination unit, in an alternating manner.

Further preferably, the applied voltage determination unit determines the two values so that a difference between the two values is a minimum.

Preferably, the determination unit determines an optimal frequency for the value of the amplitude of the voltage applied by the applied voltage control unit as the control frequency.

A control method of a blood pressure measurement device according to another preferred embodiment of the present invention is a control method of a blood pressure measurement device that includes a cuff that, when worn on a blood pressure measurement area, pressurizes an artery in the measurement area at the pressure of a fluid in the cuff, a piezoelectric pump that increases the pressure within the cuff, a deflating unit that reduces the pressure within the cuff, a pressure detection unit that detects the cuff pressure that is the pressure within the cuff, and a control unit.

The control method includes the steps of the control unit determining a control amplitude and a control frequency of a voltage applied to the piezoelectric pump, carrying out control so that a voltage at the control amplitude and control frequency determined by the determination unit is applied to the piezoelectric pump, and calculating a blood pressure value based on the cuff pressure detected by the pressure detection unit during inflation when the cuff pressure is increased by the piezoelectric pump. The step of carrying out control preferably controls the amplitude of the voltage in predetermined steps, and includes a step of applying, in a predetermined order, a voltage having an amplitude that is a value above the control amplitude by at least one step and a voltage having an amplitude that is a value below the control amplitude by at least one step so that the control is essentially the same as when a voltage at the determined control amplitude is applied.

According to various preferred embodiments of the present invention, a control amplitude and a control frequency of a voltage applied to the piezoelectric pump are determined, control is carried out so that a voltage at the determined control amplitude and control frequency is applied to the piezoelectric pump, and a blood pressure value is calculated based on the cuff pressure detected by the pressure detection unit during inflation when the cuff pressure is increased by the piezoelectric pump. In the control of the piezoelectric pump, the amplitude of the voltage preferably is controlled in predetermined steps, and a voltage having an amplitude that is a value above the control amplitude by at least one step and a voltage having an amplitude that is a value below the control amplitude by at least one step are applied, in a predetermined order, so that the control is essentially the same as when a voltage at the determined control amplitude is applied.

By amplitude-modulating the applied voltage, the piezoelectric pump is controlled in essentially the same manner as the case where the target voltage is applied. However, according to various preferred embodiments of the present invention, the occurrence of amplitude modulation frequency noise can be suppressed as compared to a case where the control is carried out through amplitude modulation. Furthermore, whereas pulsations in the increasing cuff pressure occur in the case where the control is carried out through amplitude modulation, the influence of pulsations can be reduced according to various preferred embodiments of the present invention. Furthermore, according to various preferred embodiments of the present invention, the same highly-precise inflation control preferably is achieved as in the case where the control is carried out through amplitude modulation.

As a result, it is possible to provide a blood pressure measurement device and a control method for such a blood pressure measurement device that, when controlling inflation using the piezoelectric pump during inflation for blood pressure measurement, increases the precision of blood pressure measurement by supressing the occurrence of noise, reducing the influence of pulsations, and controlling inflation at a high level of precision.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
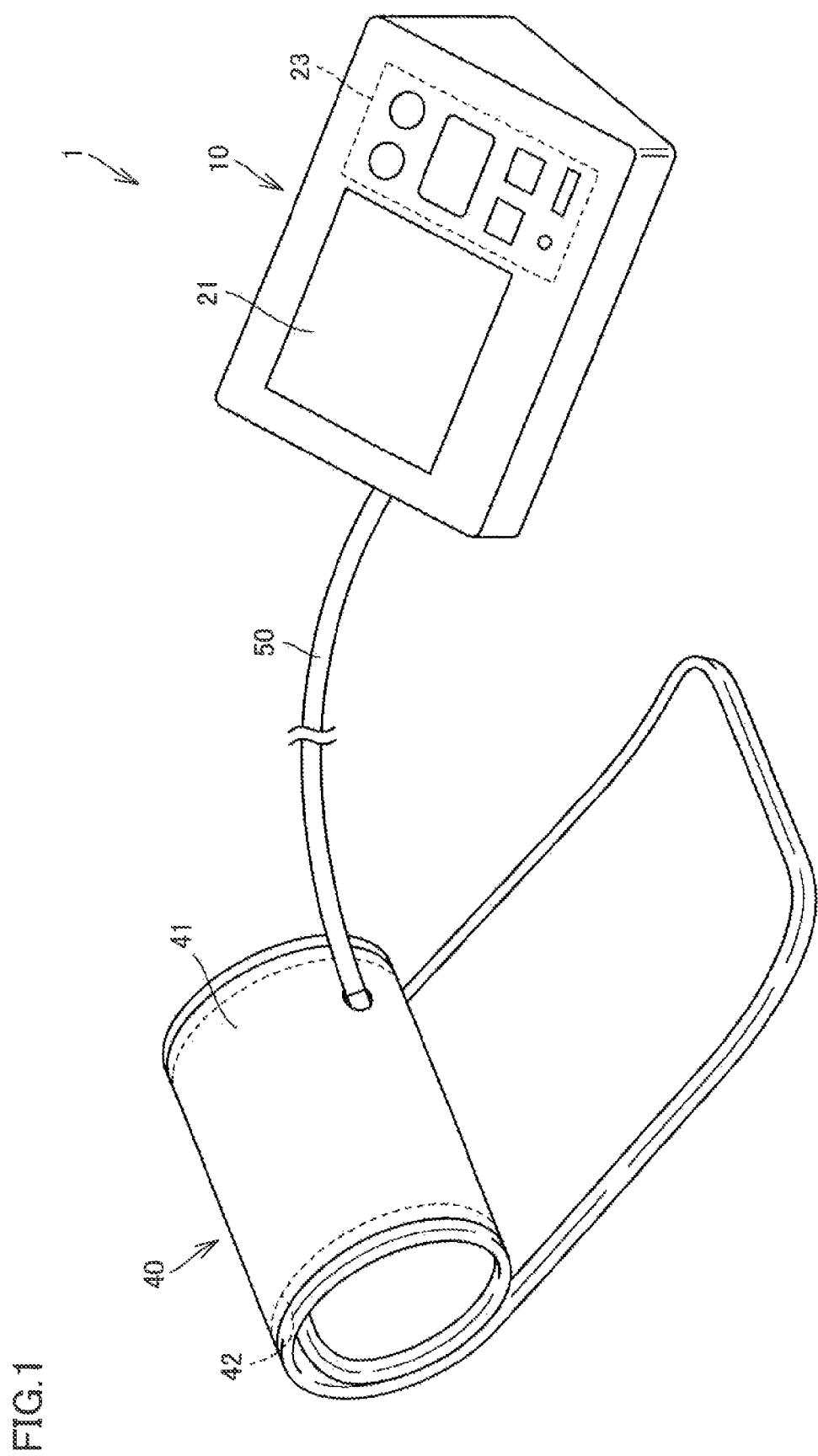
FIG. 1 is a perspective view of the outside of a blood pressure meter according to a preferred embodiment of the present invention.

Hereinafter, preferred embodiments of the present invention will be described in detail with reference to the drawings. Note that identical or corresponding elements in the drawings will be given the same reference numerals, and descriptions thereof will not be repeated.

First Preferred Embodiment

The following will describe piezoelectric pump driving control when taking an inflation-based measurement using an oscillometric blood pressure meter that takes measurements during inflation according to a preferred embodiment of the present invention.

First, the configuration of a blood pressure meter 1 according to the present preferred embodiment will be described. FIG. 1 is a perspective view of the outside of the blood pressure meter 1 according to the present preferred embodiment of the present invention. As shown in FIG. 1, the blood pressure meter 1 according to this preferred embodiment preferably includes a main body 10, a cuff 40, and an air tube 50. The main body 10 includes a box-shaped housing, and a display unit 21 and an operating unit 23 are provided on the top surface thereof. During measurement, the main body 10 is used by being placed on a placement surface such as a table or the like.

The cuff 40 primarily includes a band-shaped and bladder-shaped outer cover 41 and a pressurizing air bladder 42 that is contained in the outer cover 41 and defines and serves as a pressurizing fluid bladder; the cuff 40 preferably has an overall ring-shaped configuration. During measurement, the cuff 40 is used by being wrapped around and worn on the upper arm of a measurement subject. The air tube 50 connects the main body 10 and the cuff 40, which preferably are configured as separate entities.

Figure 2:
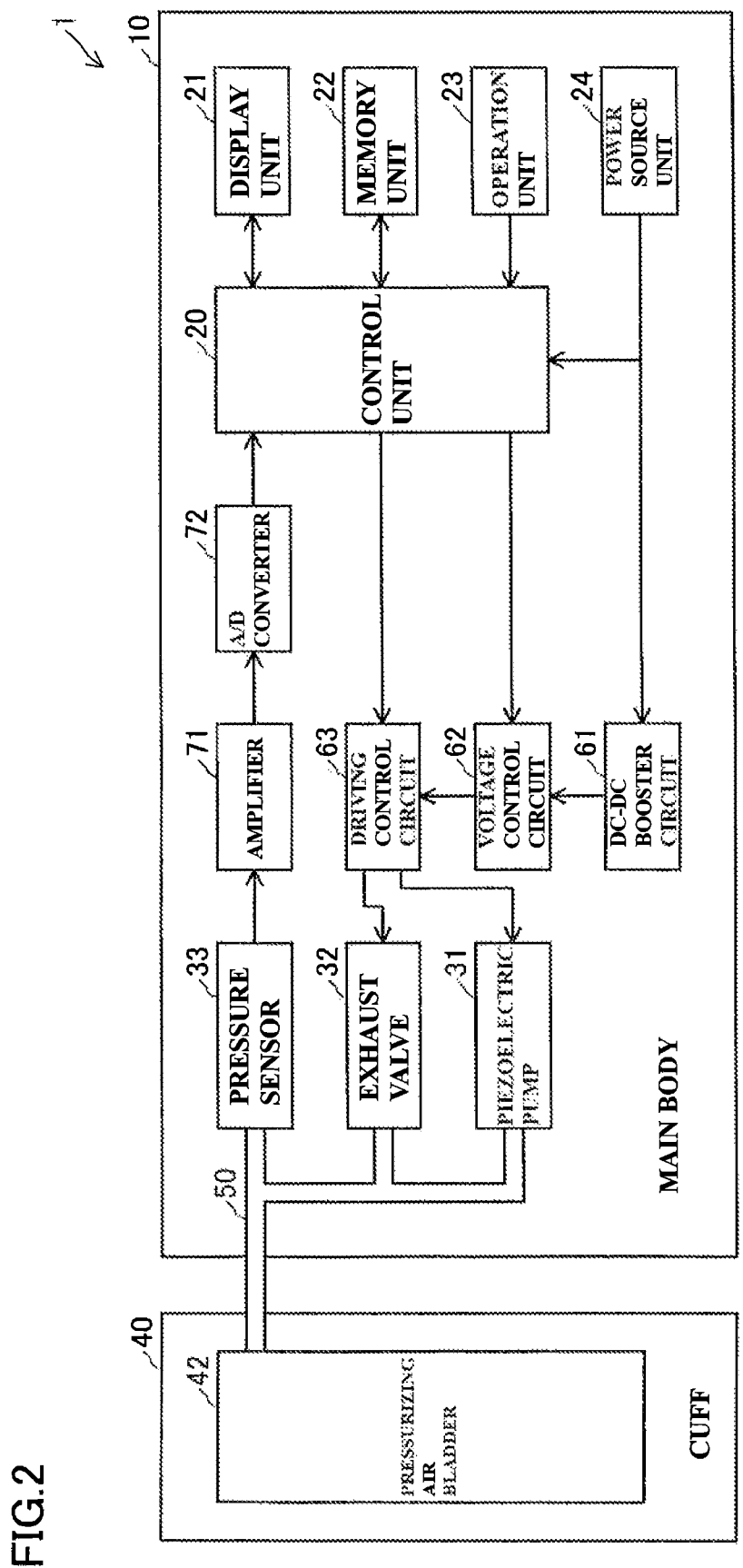
FIG. 2 is a block diagram illustrating the overall configuration of the blood pressure meter according to a preferred embodiment of the present invention.

FIG. 2 is a block diagram illustrating the overall configuration of the blood pressure meter 1 according to this preferred embodiment. As shown in FIG. 2, in addition to the display unit 21 and operating unit 23, the main body 10 includes a control unit 20, a memory unit 22, a power source unit 24, a piezoelectric pump 31, an exhaust valve 32, a pressure sensor 33, a DC-DC booster circuit 61, a voltage control circuit 62, a driving control circuit 63, an amplifier 71, and an A/D converter 72. The piezoelectric pump 31 and the exhaust valve 32 correspond to an inflation/deflation mechanism configured to increase/decrease the internal pressure of the pressurizing air bladder 42.

The pressurizing air bladder 42 pressurizes the upper arm when worn thereon, and has an interior space therein. The pressurizing air bladder 42 is connected to the piezoelectric pump 31, the exhaust valve 32, and the pressure sensor 33, respectively, via the air tube 50. As a result, the pressurizing air bladder 42 is inflated and expands under the driving of the piezoelectric pump 31; the inner pressure is held, the pressurizing air bladder 42 is deflated and contracts, and so on by controlling the driving of the exhaust valve 32.

The control unit 20 preferably includes a CPU (central processing unit), for example, and is configured and programmed to control the blood pressure meter 1 as a whole.

The display unit 21 preferably includes an LCD (liquid-crystal display), for example, and is configured to display measurement results and the like.

The memory unit 22 preferably includes a ROM (read-only memory), a RAM (random access memory), or the like, for example, and stores programs that cause the control unit 20 and the like to execute processes to measure a blood pressure value, store measurement results, and so on.

The operating unit 23 is configured to accept operations made by a measurement subject or the like and inputting such external commands into the control unit 20, the power source unit 24, and the like.

The power source unit 24 is configured to supply power to the various units of the blood pressure meter 1, such as the control unit 20 and the piezoelectric pump 31, and preferably is a battery in this preferred embodiment. However, the power source unit 24 is not limited thereto, and may receive power supplied from an external power source such as an AC outlet.

The control unit 20 is configured and programmed to input control signals to drive the piezoelectric pump 31 and the exhaust valve 32 into the voltage control circuit 62 and the driving control circuit 63, respectively, and to input blood pressure values serving as measurement results into the display unit 21 and the memory unit 22. The control unit 20 also includes a blood pressure information obtainment unit (not shown) configured to obtain a measurement subject's blood pressure value based on a pressure value detected from the pressure sensor 33 via the amplifier 71 and the A/D converter 72, and the blood pressure value obtained by the blood pressure information obtainment unit is inputted into the display unit 21 and memory unit 22 as a measurement result.

Note that the blood pressure meter 1 may also include a separate output unit that outputs a blood pressure value to an external device such as a PC (personal computer), a printer, or the like as the measurement result. For example, a serial communication line, a device that writes to various types of recording media, or the like can be used as the output unit.

The DC-DC booster circuit 61 is a circuit configured to boost the voltage of the battery that serves as the power source unit 24 to a voltage suited to the driving of the piezoelectric pump 31.

The voltage control circuit 62 controls the voltage supplied to the piezoelectric pump 31 based on a voltage value indicated by a control signal inputted from the control unit 20.

The driving control circuit 63 controls the piezoelectric pump 31 and the exhaust valve 32 based on a control signal inputted from the control unit 20. Specifically, the driving control circuit 63 controls the frequency of a current supplied to the piezoelectric pump 31 based on a control frequency indicated by the control signal inputted from the control unit 20. In addition, the driving control circuit 63 controls the exhaust valve 32 to open and close based on the control signal inputted from the control unit 20.

The piezoelectric pump 31 is configured to increase the internal pressure of the pressurizing air bladder 42 (called the "cuff pressure" as well hereinafter) by supplying air to the interior space of the pressurizing air bladder 42, and the operations thereof are controlled by the driving control circuit 63. The piezoelectric pump 31 discharges air at a predetermined flow rate by applying an AC current of a predetermined amplitude V0 at a predetermined driving frequency f0. Note that a sine wave AC may be used, a square wave AC may be used, and so on. In the following, the value of a peak-to-peak potential difference Vp-p may be used when discussing the value of a voltage applied to the piezoelectric pump 31. The amplitude is half the value of Vp-p. Relative to Vp-p, the value of the voltage changes in a value range from, for example, -Vp-p/2 to Vp-p/2.

The exhaust valve 32 is configured to hold the internal pressure in the pressurizing air bladder 42, open the interior space of the pressurizing air bladder 42 to the exterior and reduce the cuff pressure, and so on, and the operations thereof are controlled by the driving control circuit 63.

The pressure sensor 33 detects the internal pressure of the pressurizing air bladder 42 and inputs, into the amplifier 71, an output signal based on the detected pressure. The amplifier 71 amplifies the level of the signal inputted from the pressure sensor 33. The A/D converter 72 converts the signal amplified by the amplifier 71 into a digital signal and inputs the generated digital signal into the control unit 20.

Figure 3:
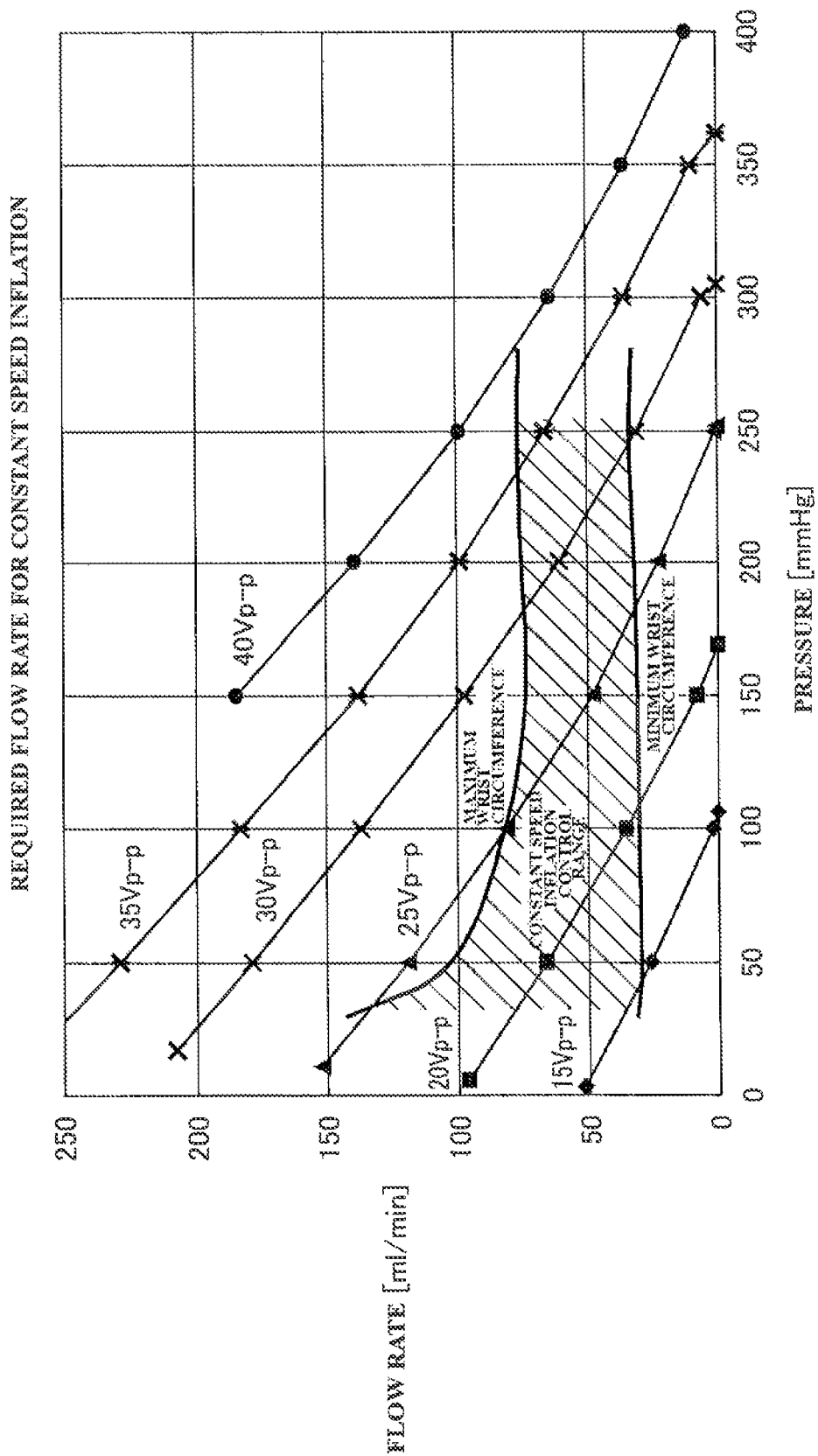
FIG. 3 is a graph illustrating a flow rate required for constant speed inflation.

FIG. 3 is a graph illustrating a flow rate required for constant speed inflation. As shown in FIG. 3, in the case where the piezoelectric pump 31 is controlled at a set voltage and the peak-to-peak potential difference of the voltage is about 15 Vp-p, the flow rate of air discharged from the piezoelectric pump 31 is approximately 50 ml/min when the cuff pressure is approximately 0 mmHg, approximately 25 ml/min when the cuff pressure is about 50 mmHg, and approximately 0 ml/min when the cuff pressure is about 110 mmHg, for example.

Likewise, when the peak-to-peak potential difference of the voltage is about 20 Vp-p, the discharge flow rate of the piezoelectric pump 31 drops from approximately 100 ml/min, to approximately 70 ml/min, to approximately 30 ml/min, to approximately 10 ml/min, to approximately 0 ml/min as the cuff pressure rises from approximately 0 mmHg, to approximately 50 mmHg, to approximately 100 mmHg, to approximately 150 mmHg, and to approximately 170 mmHg, for example.

Furthermore, in the cases where the peak-to-peak potential difference of the voltage applied to the piezoelectric pump 31 is approximately 25 Vp-p, approximately 30 Vp-p, approximately 35 Vp-p, and approximately 40 Vp-p as well, the discharge flow rate of the piezoelectric pump 31 drops as the cuff pressure rises.

Meanwhile, in the case where the circumference of a wrist, which is an area where the cuff 40 is to be worn, is a minimum length that the cuff 40 can handle, the flow rate required of the piezoelectric pump 31 when inflating the cuff 40 at a constant speed rises from approximately 30 ml/min to approximately 35 ml/min while the cuff pressure rises from about 30 mmHg to about 250 mmHg, for example.

On the other hand, in the case where the wrist circumference is a maximum length that the cuff 40 can handle, the flow rate required for constant speed inflation is approximately 145 ml/min when the cuff pressure is about 30 mmHg, but drops as the cuff pressure rises, becoming approximately 80 ml/min when the cuff pressure is about 100 mmHg, approximately 75 ml/min when the cuff pressure is about 150 mmHg, and approximately 75 ml/min when the cuff pressure is about 250 mmHg, for example.

In the case where the wrist circumference is between the minimum length and the maximum length that can be handled by the cuff 40, the cuff 40 is inflated at a constant speed by controlling the flow rate relative to the cuff pressure according to a constant speed inflation control range, indicated by the diagonal line hatching in the graph in FIG. 3.

Accordingly, in the case where the wrist circumference is the minimum, it is necessary to control the flow rate to change in the manner as the cuff pressure rises, so that in the case where the cuff 40 is inflated at a constant speed, the peak-to-peak potential difference of the voltage applied to the piezoelectric pump 31 is increased from approximately 14 Vp–p as the cuff pressure rises and reaches approximately 33 Vp–p when the cuff pressure reaches about 250 mmHg, for example.

Likewise, in the case where the wrist circumference is the maximum, it is necessary to control the flow rate to change in the manner as the cuff pressure rises, so that in the case where the cuff is inflated at a constant speed, the peak-to-peak potential difference of the voltage applied to the piezoelectric pump 31 is reduced from approximately 26 Vp–p to approximately 23 Vp–p by the time the cuff pressure reaches approximately 60 mmHg, is increased once again thereafter, and reaches approximately 37 Vp–p when the cuff pressure reaches about 250 mmHg, for example.

In this manner, in order to inflate the cuff 40 at a constant speed, it is necessary to control the voltage applied to the piezoelectric pump 31 within a given voltage amplitude range (here, a range in which the peak-to-peak potential difference is approximately 12 Vp–p to approximately 40 Vp–p, or in other words, an amplitude range of about 6 V to about 20 V). Because this is digital control, it is also necessary to increase the resolution of the control voltage in order to increase the precision of the control during constant speed inflation. However, doing so requires the use of a costly control circuit, which will lead to an increase in the manufacturing costs of the blood pressure meter 1.

Figure 4:
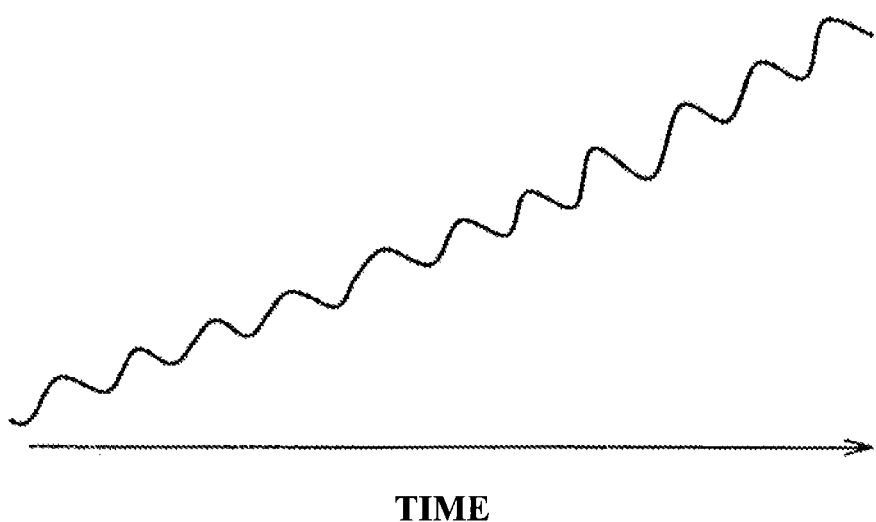
FIG. 4 is a graph illustrating changes in a cuff pressure in the case where a piezoelectric pump control voltage is AM-modulated.

FIG. 4 is a graph illustrating changes in the cuff pressure in the case where the voltage that controls the piezoelectric pump 31 is amplitude-modulated. As shown in FIG. 4, AM-modulating the control voltage can be considered as a way to increase the resolution of the control voltage.

However, doing so causes the occurrence of pulsations in the rising cuff pressure, as indicated by the graph. Such pulsations have a negative effect on the blood pressure measurement performed by the blood pressure meter 1 (worsening the measurement precision, for example). Furthermore, noise will be produced if the pulsations have a frequency in the auditory range. The volume of the noise will increase as the amplitude of the pulsations increases as well.

Figure 5:
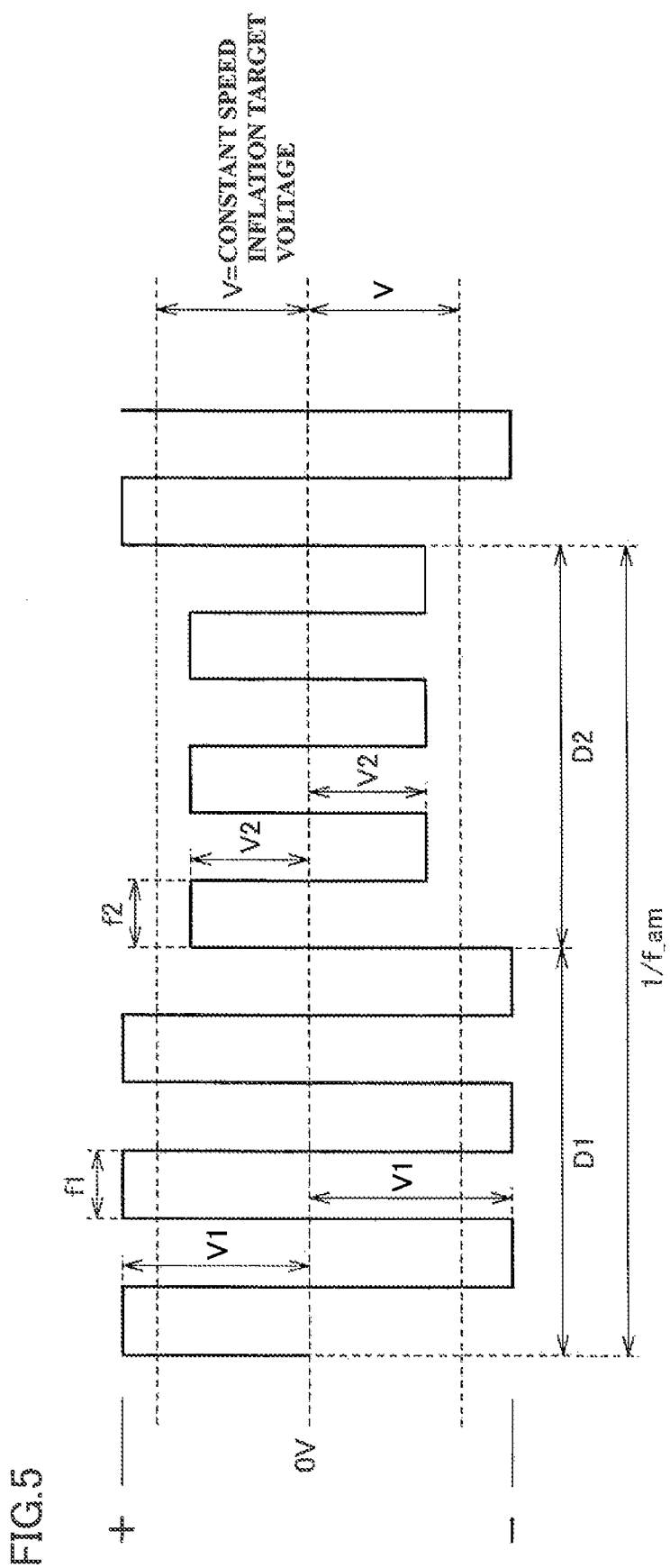
FIG. 5 is a diagram illustrating the concept of piezoelectric pump voltage control according to a preferred embodiment of the present invention.

FIG. 5 is a diagram illustrating the concept of voltage control for the piezoelectric pump 31 according to a preferred embodiment of the present invention. As shown in FIG. 5, in the blood pressure meter 1 according to this preferred embodiment, the value of the amplitude of the voltage that can be controlled is changed in steps in order to realize digital control of the voltage and so on applied to the piezoelectric pump 31. For example, in the case where a control step is equivalent to about 1 V, and the amplitude V0 of a target voltage is about 20.3 V, for example, about 20 V, about 21 V, or the like preferably is applied to the piezoelectric pump 31, but 20.3 V cannot be applied to the piezoelectric pump 31.

Note that in the case where the control resolution is about 10 bits from about 10 V to about 40 V, the control can be carried out in control steps of approximately 30 mV, whereas in the case where the control resolution is about 5 bits, the control can be carried out in control steps of approximately 1 V.

According to a preferred embodiment of the present invention, in such a case, a period corresponding to a ratio D1 of a given cycle 1/f_am is driven at a driving voltage having an amplitude V1 and an optimal frequency f1 for that driving voltage having an amplitude V1, and a period corresponding to a ratio D2 is driven at a driving voltage having an amplitude V2 and an optimal frequency f2 for that driving voltage having an amplitude V2; this controls the piezoelectric pump 31 so that air is discharged at a flow rate equivalent to the case of driving at the target voltage having the amplitude V0.

In this preferred embodiment, the amplitudes V1 and V2 of the driving voltage and duty ratios D1 and D2 are preferably determined so that V0=V1×D1+V2×D2 (where V2≤V0≤V1), and D1+D2=1.

Note that f_am is a frequency approximately the same as the frequency of the AM modulation (amplitude modulation) as described with reference to FIG. 4, and is a value from, for example, approximately 30 Hz to approximately 200 Hz; because the pulse wave component of a blood pressure is contained in frequencies below about 30 Hz, it is necessary for f_am to be a frequency greater than about 30 Hz, but may be another frequency as long as it is a frequency that is lower than the driving frequency of the piezoelectric pump (for example, a value near about 20 kHz).

Although the control becomes more responsive as the value of f_am increases, this also increases the processing burden on the control unit 20, and thus the value of f_am is determined based on the processing speed of the control unit 20.

Furthermore, noise caused by pulsations can be suppressed, the volume of such noise can be reduced, and so on by ensuring as small a difference between V1 and V2 as possible.

For example, in the case where the target voltage amplitude V0=20.3 V, V1=21V, and V2=20V, V0=V1×D1+V2×D2 and D1+D2=1, and thus the duty ratios D1 and D2 are calculated as approximately 0.3 and approximately 0.7, respectively.

Likewise, in the case where the target voltage amplitude V0=20.5V and the duty ratios D1 and D2 are both fixed at 0.5, V0=V1×D1+V2×D2 and D1+D2=1, and thus V1+V2=41. In this case, V1 and V2 can take on a variety of combinations; for example, V1 may be 29 V and V2 may be 12 V, V1 may be 22 V and V2 may be 19 V, and so on. However, because it is preferable for the difference between V1 and V2 to be as low as possible as mentioned above, the latter combination is desirable.

Figure 6:
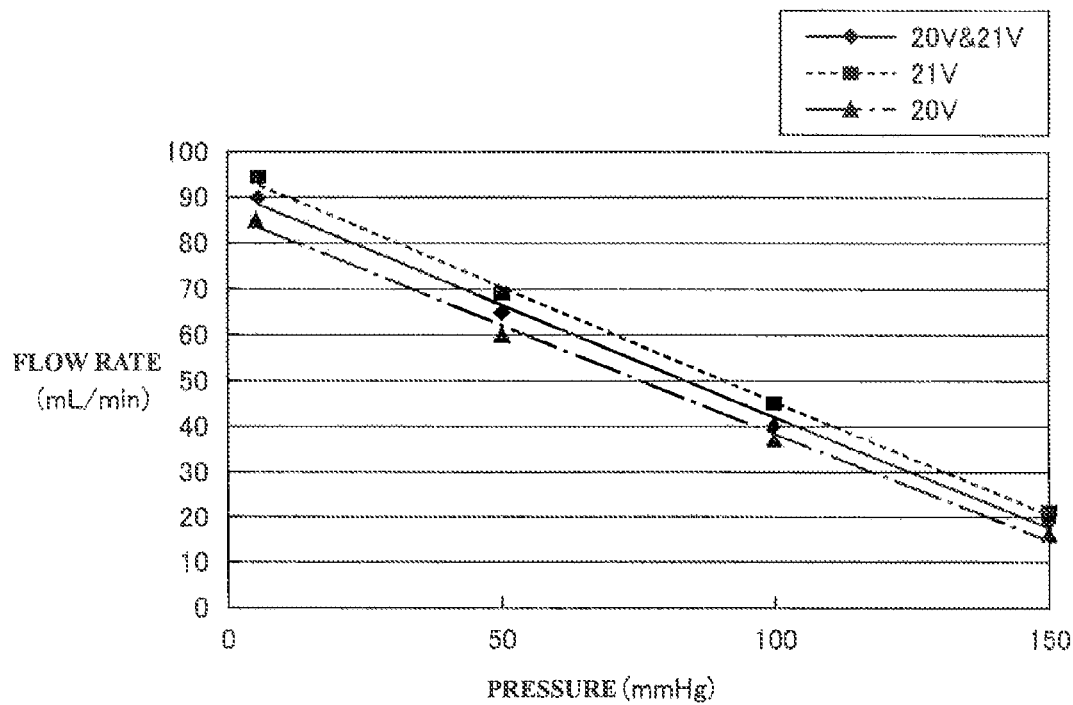
FIG. 6 is a graph illustrating a control result in the case where a piezoelectric pump undergoes voltage control according to a preferred embodiment of the present invention.

FIG. 6 is a graph illustrating a control result in the case where the piezoelectric pump 31 undergoes voltage control according to this preferred embodiment of the present invention. As shown in FIG. 6, the dot-dash line graph and the broken line graph indicate changes in the discharge flow rate of the piezoelectric pump 31 during inflation in the case where the piezoelectric pump 31 is driven at approximately 20 V and approximately 21 V, respectively, for example.

Meanwhile, the solid line graph indicates changes in the discharge flow rate of the piezoelectric pump 31 during inflation in the case where the target voltage is about 20.5 V and the piezoelectric pump 31 is driven while switching the duty ratio 50% between about 20 V and about 21 V, for example. It can be seen that in the case where the target voltage is about 20.5 V and control is carried out while switching between about 20 V and about 21 V in this manner, a discharge flow rate that is exactly between that obtained through about 20 V driving and that obtained through about 21 V driving is achieved.

Figure 7:
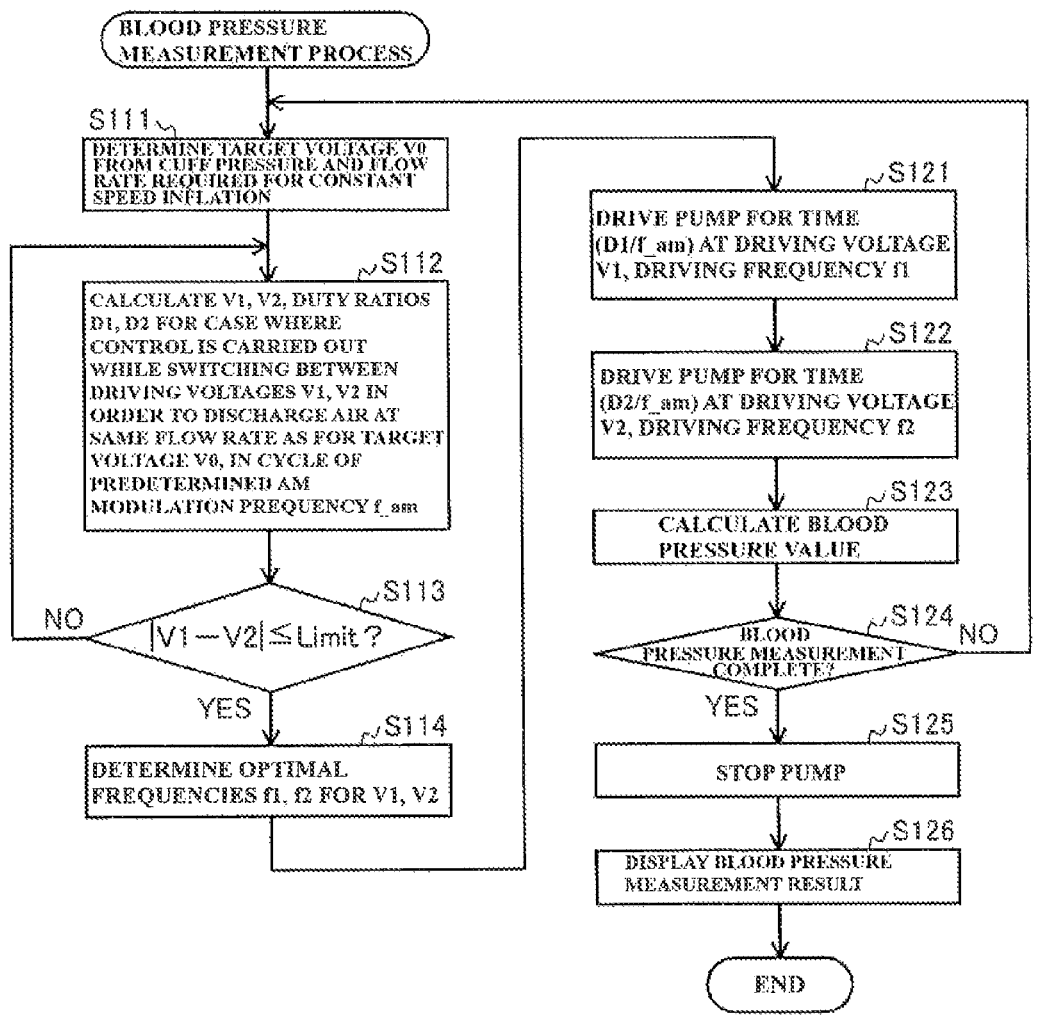
FIG. 7 is a flowchart illustrating the flow of a blood pressure measurement process executed by the blood pressure meter according to a preferred embodiment of the present invention.

FIG. 7 is a flowchart illustrating the flow of a blood pressure measurement process executed by the blood pressure meter 1 according to the first preferred embodiment. As shown in FIG. 7, in step S111, the control unit 20 determines the amplitude V of the target voltage for the piezoelectric pump 31 based on data, stored in advance in the memory unit 22 and indicated by the graphs shown in FIG. 3, of a wrapping state of the cuff 40 (the wrist circumference, whether the cuff 40 is wrapped tightly or loosely), the current cuff pressure, and the flow rate required for constant speed inflation.

Next, in step S112, the control unit 20 calculates V1 and V2 and the duty ratios D1 and D2 for the case where control is carried out while switching between the driving voltages V1 and V2, in order to discharge air at the same flow rate as for the target voltage V0, in a cycle 1/f_am of a predetermined AM modulation frequency f_am, according to the method illustrated in FIG. 5.

In step S113, the control unit 20 determines whether or not V1 and V2 calculated in step S112 fulfill the relationship |V1−V2|≤Limit, or in other words, whether or not the difference between V1 and V2 is less than or equal to a Limit. In the case where it is determined that the difference is not less than or equal to the Limit (that is, in the case where a determination of NO is made in step S113), the control unit 20 returns the processing being executed to the process in step S112.

On the other hand, in the case where it is determined that the relationship |V1−V2| Limit is fulfilled (that is, in the case where a determination of YES is made in step S113), in step S114, the control unit 20 determines the optimal frequencies f1 and f2 for V1 and V2, respectively, calculated in step S112, based on characteristic data of the piezoelectric pump 31 stored in advance in the memory unit 22. Here, although the optimal frequencies are frequencies that enable air to be discharged at a maximum flow rate, the optimal frequencies may be frequencies that achieve a maximum pump efficiency.

Next, in step S121, a signal indicating a voltage value is sent to the voltage control circuit 62 and a signal indicating a driving frequency is sent to the driving control circuit 63 so as to drive the piezoelectric pump 31 at the driving voltage V1 calculated in step S112 and the driving frequency f1 calculated in step S114 for a time D1/f_am.

Next, in step S122, a signal indicating a voltage value is sent to the voltage control circuit 62 and a signal indicating a driving frequency is sent to the driving control circuit 63 so as to drive the piezoelectric pump 31 at the driving voltage V2 calculated in step S112 and the driving frequency f2 calculated in step S114 for a time D2/f_am.

Next, in step S123, the control unit 20 calculates a blood pressure value preferably according to a conventional method based on changes in the cuff pressure detected by the pressure sensor 33 and indicated by a signal inputted into the control unit 20 via the amplifier 71 and the A/D converter 72.

Then, in step S124, the control unit 20 determines whether or not the blood pressure measurement is complete. In the case where it is determined that the blood pressure measurement is not complete (that is, in the case where a determination of NO is made in step S124), the control unit 20 returns the processing being executed to the process in step S111.

On the other hand, in the case where it is determined that the blood pressure measurement is complete (that is, in the case where a determination of YES is made in step S124), in step S125, the control unit 20 controls the voltage control circuit 62 and the driving control circuit 63 to stop driving the piezoelectric pump 31.

Next, in step S126, the control unit 20 controls the display unit 21 to display the blood pressure measurement result. After step S126, the control unit 20 ends the blood pressure measurement process.

Second Preferred Embodiment

Figure 8:
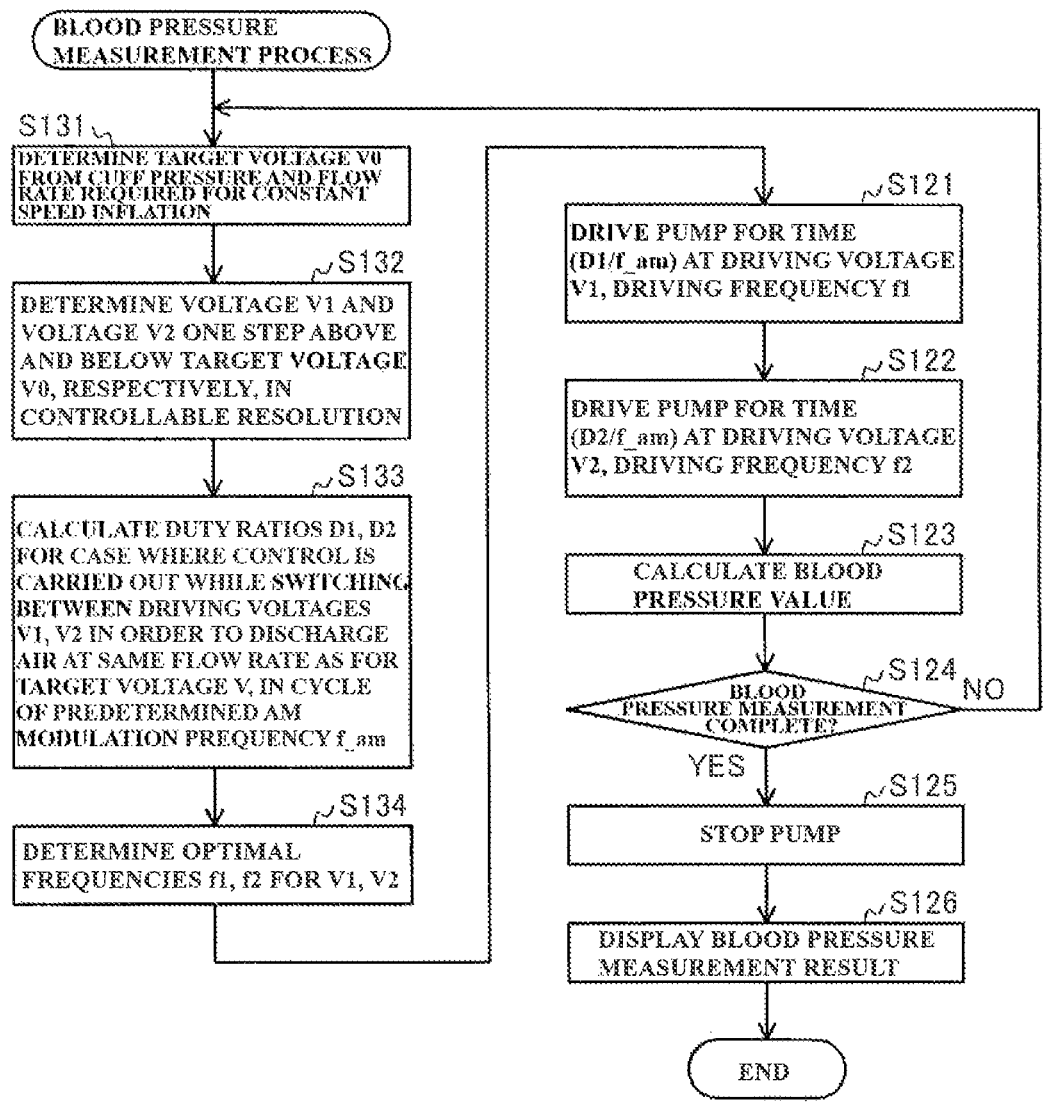
FIG. 8 is a flowchart illustrating the flow of a blood pressure measurement process executed by the blood pressure meter according to a preferred embodiment of the present invention.

FIG. 8 is a flowchart illustrating the flow of a blood pressure measurement process executed by the blood pressure meter 1 according to a second preferred embodiment of the present invention. As shown in FIG. 8, step S131 performs the same process as that performed in step S111 shown in FIG. 7 and described in the first preferred embodiment, and thus redundant descriptions will not be repeated.

Next, in step S132, the control unit 20 determines a voltage V1 one step above and a voltage V2 one step below the target voltage V0 calculated in step S131, according to the controllable resolution. For example, in the case where the resolution can be controlled in 1 V steps and the target voltage V0=20.3, V1=21V and V2=20V.

Next, in step S133, the control unit 20 calculates the duty ratios D1 and D2 for the case where control is carried out while switching between the driving voltages V1 and V2 determined in step S132, in order to discharge air at the same flow rate as for the target voltage V0, in a cycle 1/f_am of a predetermined AM modulation frequency f_am, according to the method illustrated in FIG. 5.

Then, in step S134, the control unit 20 determines the optimal frequencies f1 and f2 for V1 and V2, respectively, calculated in step S132, based on the characteristic data of the piezoelectric pump 31 stored in advance in the memory unit 22.

The processes from step S121 to step S126 are the same as the corresponding processes illustrated in FIG. 7, and thus redundant descriptions thereof will not be repeated.

The blood pressure meter 1 according to the preferred embodiments described above achieves effects such as those described below.

The blood pressure meter 1 includes the cuff 40 that is configured such that, when worn on a blood pressure measurement area, pressurizes an artery in the measurement area at the pressure of a fluid therein, the piezoelectric pump 31 configured to increase the pressure within the cuff 40, the exhaust valve 32 configured to reduce the pressure within the cuff 40, the pressure sensor 33 configured to detect the cuff pressure that is the pressure within the cuff 40, and the control unit 20.

The control unit 20 is configured and programmed to determine a control amplitude and a control frequency of the voltage applied to the piezoelectric pump 31 as indicated in step S111 to step S114 of FIG. 7 and step S131 to step S134 in FIG. 8; carry out control so that voltages at the determined control amplitudes V1 and V2 and control frequencies f1 and f2 are applied to the piezoelectric pump 31 as indicated in step S121 and step S122 in FIGS. 7 and 8; and calculate a blood pressure value based on the cuff pressure detected by the pressure sensor 33 during inflation when the cuff pressure is increased by the piezoelectric pump 31 as indicated in step S123 in FIGS. 7 and 8. In addition, the control unit 20 preferably is configured and programmed to control the amplitude of the voltage in predetermined steps, and applies, in a predetermined order, a voltage having an amplitude that is a value V1 over the control amplitude by at least one step and a voltage having an amplitude that is a value V2 below the control amplitude by at least one step so that the output of the piezoelectric pump 31 is approximately the same as when a voltage at the determined control amplitude V0 is applied, as indicated in step S111 and step S112 in FIG. 7, step S131 to step S133 in FIG. 8, and step S121 and step S122 in FIGS. 7 and 8.

By AM-modulating the applied voltage, the piezoelectric pump 31 preferably is controlled so that the discharge flow rate is essentially the same as the case where the target voltage is applied. However, with the blood pressure meter 1 according to the preferred embodiments, the occurrence of AM modulation frequency noise can be suppressed as compared to a case where the control is carried out through AM modulation. Furthermore, whereas pulsations in the increasing cuff pressure occur in the case where the control is carried out through AM modulation, the influence of pulsations can be reduced or prevented with the blood pressure meter 1 according to the preferred embodiments of the present invention. Furthermore, with the blood pressure meter 1 according to these preferred embodiments of the present invention, the same highly-precise inflation control is achieved as in the case where the control is carried out through AM modulation.

As a result, when controlling inflation using the piezoelectric pump 31 during inflation for the blood pressure measurement, the precision of blood pressure measurement is increased by suppressing the occurrence of noise, reducing the influence of pulsations, and controlling inflation at a high level of precision.

In the second preferred embodiment of the present invention, the control unit 20 preferably is configured and programmed to apply voltages having two amplitude values in an alternating manner, as indicated by step S121 and step S122 in FIG. 8. The two values are a value V1 a predetermined step above and a value V2 a predetermined step below the determined control amplitude V0, respectively (where the "predetermined step" is 1 in the second preferred embodiment). Meanwhile, the control unit 20 determines, based on the determined control amplitude V0 and the two values V1 and V2, ratios of time D1 and D2 for which the voltages at the two values V1 and V2 are applied in an alternating manner so that the output of the piezoelectric pump 31 is essentially the same as in the case where a voltage at the control amplitude V0 is applied, as indicated in step S133 of FIG. 8. The control unit 20 then applies the voltages having two amplitude values V1 and V2 according to the determined ratios of time D1 and D2, as indicated in step S121 and step S122 of FIG. 8.

By doing so, the values V1 and V2 that are the same predetermined number above and below, respectively, are determined, and thus the amplitude of the applied voltages is determined more easily than in the case where values different steps above and below are determined.

Furthermore, the control unit 20 applies the voltages so that a difference between the two values V1 and V2 is a minimum, as indicated in step S132, step S121, and step S122 of FIG. 8.

As a result, noise caused by pulsations can be suppressed, the volume of such noise can be reduced, and so on.

The control unit 20 preferably is configured and programmed to apply the voltages having the determined two amplitude values V1 and V2 in an alternating manner at the same ratio of time, namely D1=D2=0.5, as indicated in FIG. 5 and described in the first preferred embodiment. The control unit 20 preferably determines, based on the determined control amplitude V0, the value V1 a step above the control amplitude V0 and the value V2 a step below the control amplitude V0 so that the output of the piezoelectric pump 31 is essentially the same as in the case where a voltage at the control amplitude V0 is applied, as indicated in step S112 of FIG. 7. Then, the control unit 20 applies the determined voltages having two amplitude values V1 and V2 in an alternating manner, as indicated in step S121 and step S122 in FIG. 7.

In step S113 of FIG. 7, the control unit 20 determines whether or not the difference between the two values V1 and V2 is less than or equal to a predetermined value Limit, and in the case where the difference is not less than or equal to the Limit, re-determines the two values V1 and V2 so that the difference between the two values V1 and V2 is less than or equal to the Limit. Furthermore, the control unit 20 preferably determines the two values so that a difference between the two values is a minimum.

Noise caused by pulsations can be suppressed, the volume of such noise can be reduced, and so on in both the case where the difference between the two values V1 and V2 is less than or equal to the Limit and the case where the difference is set to a minimum.

The control unit 20 preferably is configured and programmed to determine optimal frequencies f1 and f2 for the values V1 and V2 of the amplitude of the applied voltages as the control frequency, as indicated in step S114 of FIG. 7 and step S134 of FIG. 8.

As a result, the optimal frequencies for the respective voltages is applied, even in the case where the voltage is applied while switching among a plurality of amplitudes. Accordingly, the piezoelectric pump 31 is controlled in an optimal manner regardless of the timing.

Next, variations of the preferred embodiments of the present invention will be described.

The preferred embodiments preferably use air as the fluid supplied to the cuff 40 from the piezoelectric pump 31, for example. However, the fluid supplied to the cuff 40 from the piezoelectric pump 31 is not limited thereto, and another fluid, such as a liquid or a gel, may be used as well. The present invention is also not limited to a fluid, and may instead use uniform particles such as microbeads or the like.

Although the preferred embodiments describe the size of the measurement area as preferably corresponding to the wrist circumference, the present invention is not limited thereto, and different sizes may preferably be used for different measurement areas. For example, in the case where the measurement area is the arm, the size is the circumference of the arm.

As indicated in FIGS. 7 and 8, the preferred embodiments describe the cycle at which the control amplitude V0 is determined and control parameters such as V1, V2, f1, and f2 are updated and the cycle at which the blood pressure value is calculated as preferably being every cycle D1/f_am+D2/f_am=1/f_am, or in other words, every single cycle of duty control, for example. However, the present invention is not limited thereto, and the cycle for updating the control parameters and calculating the blood pressure value may be set to a plurality of duty control cycles.

In the first preferred embodiment, in step S112 of FIG. 7, the voltage amplitudes V1 and V2 are preferably determined first and the duty ratios D1 and D2 may then be calculated for the amplitudes V1 and V2, or the duty ratios D1 and D2 may be determined first and the voltage amplitudes V1 and V2 may then be calculated for the duty ratios D1 and D2.

The preferred embodiments describe a case where the control is carried out preferably while switching between the two voltage amplitudes V1 and V2. However, the present invention is not limited thereto, and the control may be carried out while switching among three or more voltage amplitudes. For example, control may be carried out while switching among four voltage amplitudes, namely approximately 19 V, approximately 20 V, approximately 21 V, and approximately 22 V, in order at a duty ratio of about 0.25, so that the fluid can be ejected at the same flow rate as when the target voltage has an amplitude of about 20.5 V.

In the second preferred embodiment, as described in step S132 of FIG. 8, the voltage V1 one step above in the controllable resolution and the voltage V2 one step below in the controllable resolution relative to the target voltage V0 preferably are determined. As a result the voltage is preferably applied so that the difference between V1 and V2 is a minimum. However, the present invention is not limited thereto, and the voltages may be determined two or more steps above and below in the controllable resolution relative to the target voltage V0. For example, a voltage V1 of about 25V and a voltage V2 of about 16V are determined five steps above and five steps below, respectively, a target voltage V0 of about 20.3 V, in the controllable resolution. Noise caused by pulsations will not worsen as long as the difference between V1 and V2 is less than or equal to the Limit.

The preferred embodiments describe the blood pressure meter 1 as an apparatus invention. However, the present invention is not limited thereto, and is also a control method of the blood pressure meter 1. The present invention is also a control program for the blood pressure meter 1.

Note that the preferred embodiments disclosed above are to be understood as being in all ways exemplary and in no way limiting. The scope of the present invention is defined not by the descriptions but by the scope of the appended claims, and all changes that fall within the same essential spirit as the scope of the claims are intended to be included therein as well.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A blood pressure measurement device comprising:
    a cuff configured to, when worn on a blood pressure measurement area, pressurize an artery in the blood pressure measurement area at a pressure of a fluid in the cuff;
    a piezoelectric pump configured to increase the pressure within the cuff;
    a deflating unit configured to reduce the pressure within the cuff;
    a pressure detection unit configured to detect a cuff pressure that is the pressure within the cuff; and
    a control unit configured and programmed to include:
        a determination unit configured and programmed to determine a control amplitude and a control frequency of a voltage applied to the piezoelectric pump;
        an applied voltage controller configured and programmed to perform control so that a voltage at the control amplitude and the control frequency determined by the determination unit is applied to the piezoelectric pump; and
        a blood pressure measurement unit configured and programmed to calculate a blood pressure value based on the cuff pressure detected by the pressure detection unit during inflation when the cuff pressure is increased by the piezoelectric pump; wherein
    the applied voltage controller is configured and programmed to control the amplitude of the voltage in predetermined steps, and to apply, in a predetermined order, a voltage having an amplitude that is a value above the control amplitude by at least one step and a voltage having an amplitude that is a value below the control amplitude by at least one step so that an output of the piezoelectric pump is approximately the same as when a voltage at the control amplitude determined by the determination unit is applied.

2. The blood pressure measurement device according to claim 1, wherein
    the applied voltage controller is configured and programmed to apply voltages with two amplitude values in an alternating manner;
    the two amplitude values include a value a predetermined step above and a value a predetermined step below the control amplitude determined by the determination unit, respectively;
    the control unit is further configured and programmed to include an application ratio determination unit that is configured and programmed to, based on the control amplitude determined by the determination unit and the two amplitude values, determine a ratio of time for which the voltages at the two amplitude values are applied in an alternating manner so that the output of the piezoelectric pump is approximately the same as in a case where the voltage at the control amplitude is applied; and
    the applied voltage controller is configured and programmed to apply the voltages with the two amplitude values according to the ratio of time determined by the application ratio determination unit.

3. The blood pressure measurement device according to claim 2, wherein the applied voltage controller is configured and programmed to apply the voltages so that a difference between the two amplitude values is a minimum.

4. The blood pressure measurement device according to claim 1, wherein
    the applied voltage controller is configured and programmed to apply the voltages with the two amplitude values determined by the determination unit in an alternating manner at a same ratio of time;
    the control unit is further configured and programmed to include an applied voltage determination unit that, based on the control amplitude determined by the determination unit, determines the value a step above the control amplitude and the value a step below the control amplitude so that the output of the piezoelectric pump is approximately the same as in a case where the voltage at the control amplitude is applied; and
    the applied voltage controller is configured and programmed to apply the voltages with the two amplitude values, determined by the applied voltage determination unit, in an alternating manner.

5. The blood pressure measurement device according to claim 4, wherein the applied voltage determination unit is configured and programmed to determine the two amplitude values so that a difference between the two amplitude values is a minimum.

6. A control method for a blood pressure measurement device including a cuff that, when worn on a blood pressure measurement area, pressurizes an artery in the blood pressure measurement area at a pressure of a fluid in the cuff, a piezoelectric pump that increases the pressure within the cuff, a deflating unit that reduces the pressure within the cuff, a pressure detection unit that detects a cuff pressure that is the pressure within the cuff, and a control unit, the control method comprising the steps performed by the control unit including:

determining a control amplitude and a control frequency of a voltage applied to the piezoelectric pump;

carrying out control so that a voltage at the control amplitude and the control frequency determined by the determination unit is applied to the piezoelectric pump; and calculating a blood pressure value based on the cuff pressure detected by the pressure detection unit during inflation when the cuff pressure is increased by the piezoelectric pump; wherein the step of carrying out control is performed to control the control amplitude of the voltage in predetermined steps, and includes a step of applying, in a predetermined order, a voltage having an amplitude that is a value above the control amplitude by at least one step and a voltage having an amplitude that is a value below the control amplitude by at least one step so that an output of the piezoelectric pump is approximately the same as when a voltage at the determined control amplitude is applied.

\* \* \* \* \*